United States Patent [19]

Salmond

[11] 4,206,131
[45] Jun. 3, 1980

[54] COMPOUNDS AND PROCESS

[75] Inventor: William G. Salmond, Mattawan, Mich.

[73] Assignee: The Upjohn Company, Kalamazoo, Mich.

[21] Appl. No.: 916,921

[22] Filed: Jun. 19, 1978

[51] Int. Cl.$^2$ ............................................. C07J 9/00
[52] U.S. Cl. ................................................ 260/397.2
[58] Field of Search .................................... 260/397.2

[56] References Cited

U.S. PATENT DOCUMENTS 3,993,675  11/1976  Vskokovic et al. ............... 260/397.2

OTHER PUBLICATIONS

"Steroids", vol. 30, No. 2, Aug. 1977, article by Pelc. pp. 193–201.

*Primary Examiner*—Elbert L. Roberts
*Attorney, Agent, or Firm*—Sidney B. Williams, Jr.

[57] ABSTRACT

A process for preparing 1α-hydroxylated calciferols is described. Intermediates used in the process are also provided.

34 Claims, No Drawings

COMPOUNDS AND PROCESS

BACKGROUND OF THE INVENTION

1. Field of the Invention

This invention concerns the preparation of 1-hydroxycalciferol (that is 1-hydroxy Vitamin D) derivatives with special reference to the 1α-hydroxy derivatives. These compounds are well known to be highly active in combating many disorders of calcium metabolism.

2. Prior Art

Numerous preparation of 1α- and 1β-hydroxy calciferol derivatives have been described. A brief list includes: 1α-hydroxycholecalciferol [DeLuca et al. U.S. Pat. No. 3,741,996; Barton et al. J.A.C.S. 95, 2748 (1973); Fürst et al., Helvetica 56, 1708 (1973)]; 1β-cholecalciferol [Mazur et al., J.O.C. 42, 3597 (1977); DeLuca et al., Chem. Comm., 890 (1977)]; 1α,25-dihydroxy cholecalciferol [DeLuca et al., Tetrahedron Letters, 4147 (1972); Barton et al., Chem. Comm. 203 (1974); Uskokovic et al., U.S. Pat. No. 3,993,675]; 1β,25-dihydroxycholecalciferol [DeLuca et al., Chem. Comm., 890 (1977)]; 1α-hydroxyergocalciferol [DeLuca et al., Science 186, 1038 (1974)]; 1α,25-dihydroxyergocalciferol [DeLuca et al., Biochemistry 14, 1250 (1975)]; 1α,24 R and S-dihydroxycholecalciferols [Ikekawa et al., J.C.S. Perkin 1, 1421 (1975)]; 1α,24 R and S, 25-trihydroxycholecalciferols [Ikekawa et al., Chem. Pharm. Bull., 23, 695 (1975)].

This is by no means an exhaustive list but it is representative of the major approaches to the major 1-hydroxy derivatives of calciferol. A salient feature of almost all of these syntheses is that the 1α-hydroxy calciferol is derived from its 1α-hydroxy steroidal provitamin isomer through the standard photochemical and thermal rearrangements of this system Two approaches avoid this undesirable photochemical transformation. One is that of Lythgoe et al. [J.C.S. Perkin 1, 2654 (1974)] which described a total synthesis of 1α-hydroxy-cholecalciferol. This is a lengthy synthesis and is of academic interest only not being at all suitable for large scale production, especially for the more highly substituted derivatives. The second is that of Pelc who describes the direct oxidation of cholecalciferol [Steroids 30, 193 (1977)], but the yield of the desired 1α-hydroxy-cholecalciferol is exceedingly low.

SUMMARY OF THE INVENTION

This invention pertains to a chemical process for the conversion of a calciferol derivative into its 1α-hydroxy or 1β-hydroxy-cis or trans analogs. The process comprises (1) converting derivatives of calciferol to selenium analogs. (2) oxidising the selenium analogs, and (3) converting the products of the oxidation to 1α- (or 1β-) hydroxy calciferols. The invention also includes intermediates formed and used in the process.

DETAILED DESCRIPTION OF THE INVENTION

The novel process, briefly described above, can be illustrated schematically as follows:

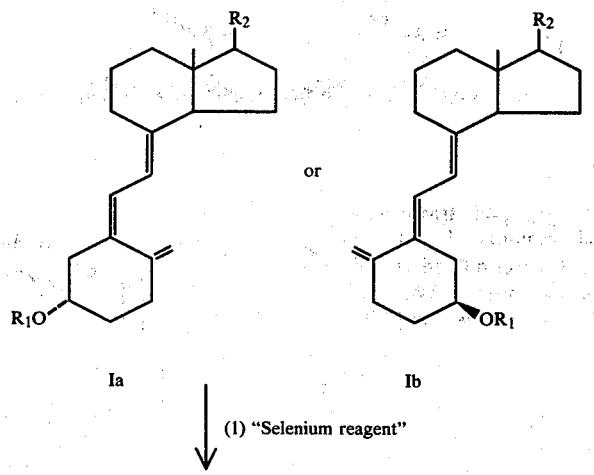

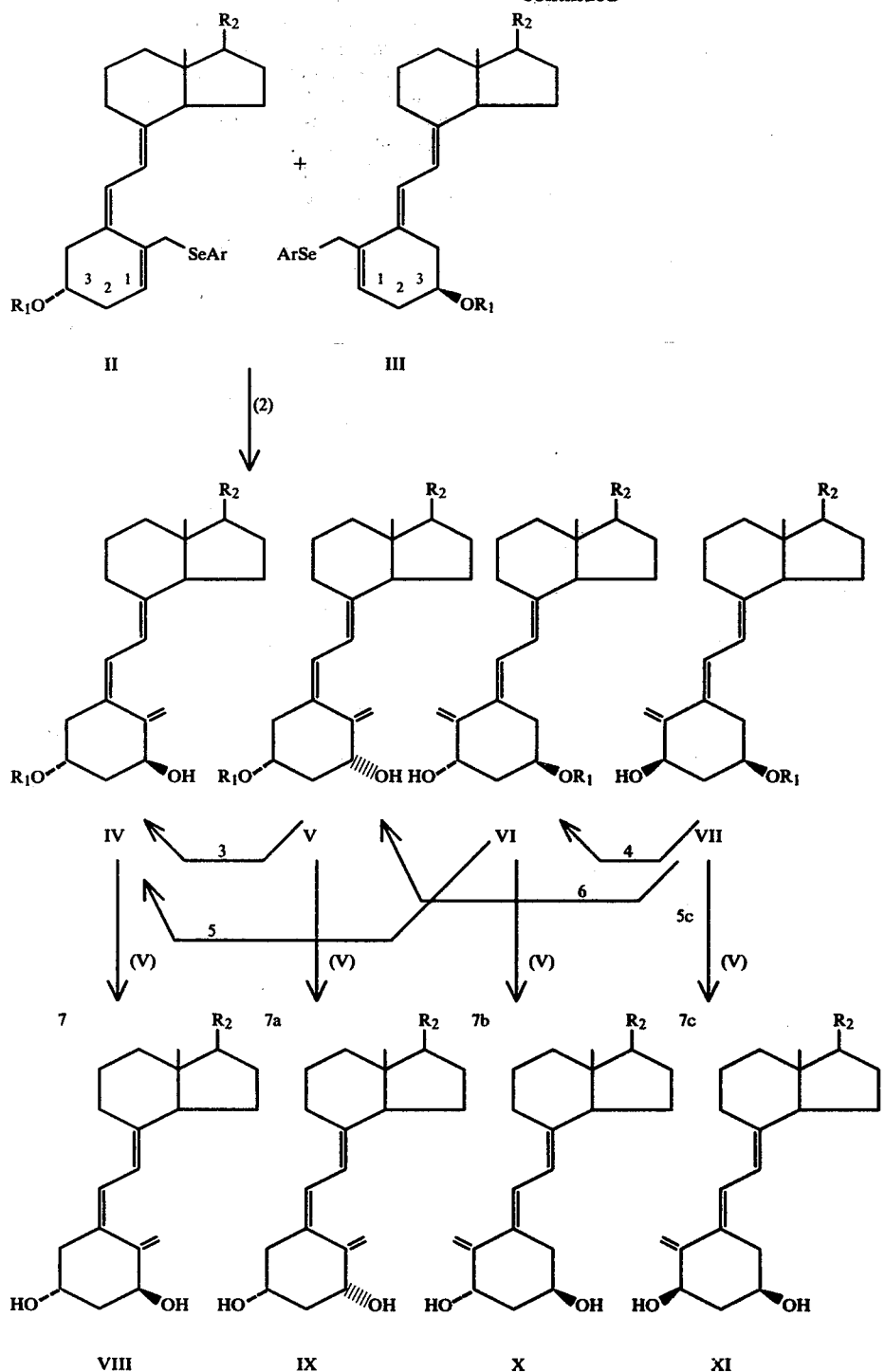
wherein $R_1$ is selected from the group consisting of hydrogen, trimethylsilyl, t-butyldimethylsilyl, phenyldimethylsilyl, acyl of from 2 to 6 carbon atoms, and aroyl wherein the aroyl group is benzoyl or substituted benzoyl; $R_2$ is selected from the group consisting of
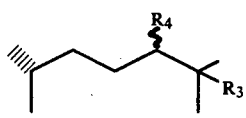
(a)
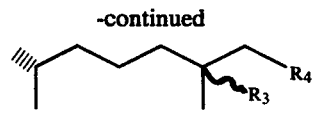
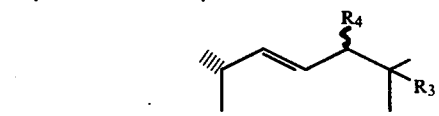

wherein R₃ is selected from the group consisting of hydrogen, hydroxy, trimethylsilyloxy, acyloxy of from 2 to 6 carbon atoms, inclusive, and aroyloxy, wherein aryl is selected from the group consisting of benzoyl and substituted benzoyl; R₄ is selected from the group consisting of hydrogen, hydroxy, trimethylsilyloxy, acyloxy of from 2 to 6 carbon atoms, inclusive and aroyloxy; and wherein R₃ and R₄ when taken together form a group selected from acetonide,

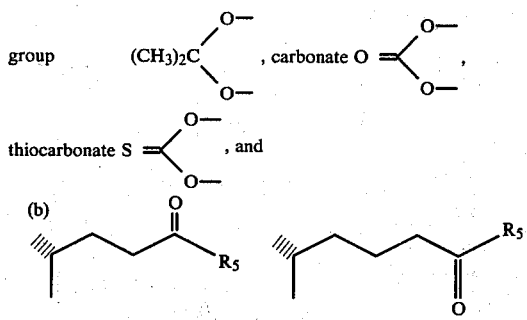

(b)

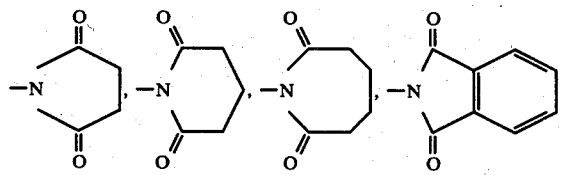

wherein R₅ is selected from the group consisting of hydrogen, methyl, hydroxyl, and lower alkoxy of from 1 to 5 carbon atoms, inclusive;

and the "selenium reagent" is selected from the group consisting of aryl selenenyl halide, ArSeX, wherein Ar is phenyl or phenyl substituted with chloro, bromo, lower alkyl, lower alkoxy or nitro, and X is chlorine, bromine, fluorine or iodine, aryl seleninic anhydride, $$\text{ArSe}-\text{O}-\text{Se}-\text{Ar},$$
with O double-bonded above each Se, and Ar—Se—R₆
wherein R₆ is selected from the group consisting of

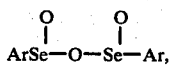

and Ar is the same as defined above.

In the foregoing designation of variable, "acyl of from 2 to 6 carbon atoms" means acetyl, propionyl, butyryl, pentynyl and hexenyl, and the isomeric forms thereof.

"Substituted phenyl" means lower alkyl, lower alkoxy, halogen, nitro and cyano substituted phenyl.

"Lower alkyl" means methyl, ethyl, propyl, butyl, pentyl and isomeric forms thereof.

"Lower alkoxy" means methoxy, ethoxy, propoxy, butoxy, pentoxy and isomeric forms thereof.

The starting cis- or trans- vitamin D materials, 1a, 1b are commercially available or can be prepared by methods described in the literature. Step 1 is conducted by reacting a compound of formula 1 with a selenium reagent having the formula described above, usually in the presence of a solvent. The amount of selenium reagent used should be between 1 and 10 moles per mole of Vitamin D compound and the reaction conducted at temperatures ranging from −80° to +100° C. for periods ranging from a few minutes to several hours, the exact conditions being determined largely by the nature of the selenium reagent used.

For example, when the selenium reagent is phenyl selenenyl chloride the reaction is conducted in the range −80° to −50° C., preferably at −68° for a period of only a few minutes with a molar ratio of 1:1. Methylene chloride is the preferred solvent although other halogenated hydrocarbons, as well as ethers may be used. After the addition of the phenyl selenenyl chloride, a base such as alkali metal alkoxides or preferably an amine such as triethylamine, diazabicyclononene or diazabicycloundecene, is added.

When the selenium reagent is an aryl seleninic anhydride, the preferred reagent is phenyl seleninic anhydride. Solvents such as benzene, toluene, halogenated hydrocarbons, alkanes, ethers may be used. The preferred solvent is chloroform, and the preferred temperature is at the boiling point. The preferred molar ratio is 1:1.

When the selenium reagent is an N-(arylselenenyl)-succinimide the preferred reagent is N-(phenylselenenyl)-succinimide. Solvents such as halogenated hydrocarbons, for example methylene chloride or chloroform, aromatic hydrocarbons, for example benzene or toluene, ethers such as tetrahydrofuran or dioxan may be used. Polar aprotic solvents such as dimethylsulfoxide, dimethylformamide, tetramethylurea or hexamethylphosphoric triamide are preferred. The molar ratio of selenium reagent to the calciferol derivative may vary from 1 to 10 although preferred is approximately 4. The temperature of the reaction may vary in the range of room temperature to 100° C., the preferred temperature range being approximately 70°–75° C.

The selenium compound III can be obtained from the reaction mixture by conventional means such as crystallization, extraction, chromatography and combinations thereof. The selenium compound II is produced in relatively small amounts and is not usually isolated pure, but rather carried on directly to the next stage of the reaction sequence.

In step 2, the next stage of the reaction sequence, compounds II and III are reacted, with an oxidizing agent, preferably in presence of a solvent. The preferred mode of conducting the oxidation is to use the purified III alone. Compound II, being more difficult to isolate than III, is usually oxidized as a mixture with III. Suitable oxidizing agents include m-chloroperoxybenzoic acid, peracetic acid and ozone, the preferred oxidant being hydrogen peroxide. Suitable solvents include methylene chloride, chloroform, dioxane and the preferred solvent in conjunction with hydrogen peroxide is tetrahydrofuran. The range of molar ratio of hydrogen peroxide to the allylic selenide III is 1 to 5, preferred being about 2.5 to 3. The temperature range for conducting the oxidation is from −40° to +45° C., the preferred range being −15° to 0° C. The reaction products IV, V, VI and VII resulting from the oxidation are recovered from the reaction mixture by conventional methods such as crystallization, extraction, distillation, chromatography and combinations thereof.

The products of the oxidation are the more desirable 1α-hydroxy derivatives and the less desirable 1β-hydroxy derivatives. Steps 3 and 4 represent methods for converting the 1β-hydroxy-derivatives to the more desirable 1α-hydroxy-derivatives by a process of epimerization for example by means of the Mislow rearrangement sequence [see Evans et al., Accounts of Chemical Research, 7, 147 (1974)] or by means of the method of Loibner et al. I, Helvetica, Vol. 59, p. 2100 (1976) and Loibner et al. II, Helvetica, Vol. 60, p. 417 (1977).

The method of converting 1β-hydroxy to the 1α-hydroxy-derivative allows a higher yield of the desirable 1α-hydroxy-derivative to be obtained, V thereby being converted to IV and VII to VI.

In step 5 the 1α-hydroxy-trans-vitamin D derivative, VI, is converted to the desired 1α-hydroxy-cis-vitamin D derivative IV by irradiation. This photochemical transformation of a trans-vitamin D derivative to the cis-vitamin is well known in the art and is based upon the brilliant pioneering studies of Havinga et al., [Rec. Trav. Chim. Pays-Bas 74, 1125 (1955)] and of Inhoffen et al. [Berichte 90, 2544 (1957); J. Chem. Soc., 385 (1959)].

It is likewise possible to isomerise a 1β-hydroxy-trans-derivative VII to the 1β-cis-derivative V as in process 6. V may then be isomerised as mentioned above to IV. However, it is preferable that VII be isomerised first to VI by process 4 and then VI isomerised photochemically by process 5 to cis-vitamin IV. In this preferred sequence VII→VI→IV, the yield of IV is optimum. In terms of the separation of IV from VI which is necessary after the photolysis of VI to IV, an equilibrium mixture being obtained, it is preferable that $R_2$ be such that the chromatographic polarity of the side chain be as low as possible. Thus if hydroxyls were present in the original vitamin in the 24, 25 and/or 26-positions, it is preferred that they be protected by a non-polar protecting group such as trimethylsilyl or acetate. In this way the ease of the chromatographic separation of IV and VI is enhanced.

When preparing compounds of formulas IV thru VII wherein $R_2$ is either

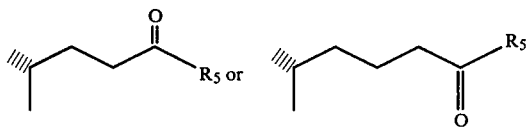

and $R_5$ is hydrogen, it is preferred to conduct the selenium reaction and the subsequent oxidation reaction on compounds wherein $R_5$ is alkyl or alkoxy and then replace the alkyl or alkoxy group with hydrogen.

In steps 7, 7a, 7b, and 7c the compounds of formulae IV, V, VI and VII are subjected to hydrolysis to yield the dihydroxy derivatives VIII, IX, X and XI respectively. The hydrolysis is accomplished by utilizing methods and reagents well known in the art. The particular reagent used will depend upon such things as the nature of the radical $R_1$. For example cold dilute hydrochloric acid can be used when $R_1$ is trimethylsilyl, and aqueous methanolic potassium hydroxide can be used when $R_1$ is benzoyl. Selection of the appropriate reagents for hydrolysis will be obvious to those skilled in the art. Although the processes 7a, 7b and 7c are easily carried out, and the compounds IX, X and XI thereby easily obtained it is, from the point of view of maximum conversion to the desired VII, that conversion to the 1α-hydroxy-cis-vitamin structure be done when the protection of the 3β-hydroxy is still intact. Paralleling processes 5 and 6 compound X may be converted to VIII and compound XI to IX, but this is less preferred because of the difficulty of separation at the A-ring dihydroxy stage.

Compounds of formula II thru VII wherein $R_2$ is the group

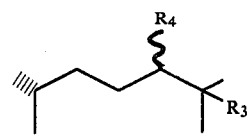

wherein $R_3$ is selected from the group consisting of acetoxy and trimethylsilyloxy and $R_4$ is hydrogen.

The following examples illustrate the inventive scope. They are intended to be illustrative of and not limitative of the invention.

PREPARATION 1

19-Phenylseleneno 9,10-secoholesta-1(10),5E,7E-triene-3β-ol, 3-benzoate

To a solution of cholecalciferol benzoate (20 g) in dry dimethylformamide (150 ml) at 65° C., and in an atmosphere of argon, is added N-phenylseleno succinimide (20 g) and azo-bis-isobutyronitrite (0.5 g), and the mixture maintained at this temperature for 4 hours. The mixture is poured into water, extracted with hexane (500 ml) and the extracts washed with a solution of sodium bicarbonate and then brine. After drying over sodium sulfate the extracts are evaporated to yield a residue which is crystallized from a mixture of acetone and methanol to yield 19-phenylseleneno 9,10-secocholesta-1(10), 5,7E-triene-3β-ol, 3-benzoate, m.p. 121°.

$[\alpha]_D(CHCl_3C=0.876)=+212°$

Analysis, Calc'd for $C_{40}H_{52}O_2Se$: C, 74.62; H, 8.14. Found: C, 74.96, H, 7.95%.

NMR (DCDl$_3$)—δ0.52s(3H); 3.78s(2H); 5.23m(1H); 5.53m(1H); 5.90 and 6.62 AB, J=12Hz, (2H); 7.07–7.63m(8H); 7.90–8.13m(2H).

Utilizing a procedure similar to that described in Preparation 1, but substituting the appropriately substituted cholecalciferol for cholecalciferol benzoate there is obtained the following compounds.

Table I

| $R_1$ | $R_2$ | Ar |
|---|---|---|
| benzoyl | ⟋⟍⟋⟍Y | phenyl |
| 2-methylbenzoyl | " | phenyl |
| 3-t-butylbenzoyl | " | phenyl |
| 4-pentylbenzoyl | " | phenyl |
| 2-methoxybenzoyl | " | phenyl |
| 4-pentoxybenzoyl | " | phenyl |
| 2-chlorobenzoyl | " | phenyl |
| 3-bromobenzoyl | " | phenyl |
| 3-fluorobenzoyl | " | phenyl |
| 4-iodobenzoyl | " | phenyl |
| 4-nitrobenzoyl | " | phenyl |
| 2-cyanobenzoyl | ⟋⟍⟋⟍OH | phenyl |
| acetyl | " | phenyl |
| propionyl | " | phenyl |
| butyryl | " | phenyl |
| pentanoyl | " | phenyl |
| benzoyl | " | phenyl |

Table I-continued

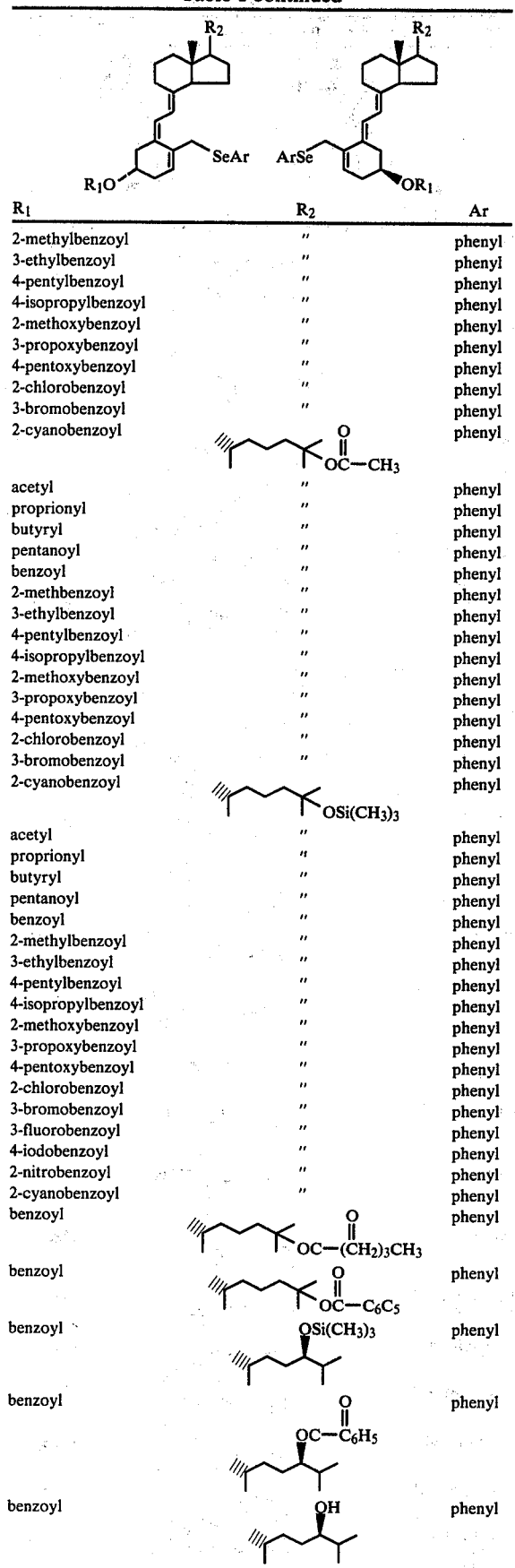

| R₁ | R₂ | Ar |
|---|---|---|
| 2-methylbenzoyl | " | phenyl |
| 3-ethylbenzoyl | " | phenyl |
| 4-pentylbenzoyl | " | phenyl |
| 4-isopropylbenzoyl | " | phenyl |
| 2-methoxybenzoyl | " | phenyl |
| 3-propoxybenzoyl | " | phenyl |
| 4-pentoxybenzoyl | " | phenyl |
| 2-chlorobenzoyl | " | phenyl |
| 3-bromobenzoyl | " | phenyl |
| 2-cyanobenzoyl | (side chain with OC(O)CH₃) | phenyl |
| acetyl | " | phenyl |
| proprionyl | " | phenyl |
| butyryl | " | phenyl |
| pentanoyl | " | phenyl |
| benzoyl | " | phenyl |
| 2-methbenzoyl | " | phenyl |
| 3-ethylbenzoyl | " | phenyl |
| 4-pentylbenzoyl | " | phenyl |
| 4-isopropylbenzoyl | " | phenyl |
| 2-methoxybenzoyl | " | phenyl |
| 3-propoxybenzoyl | " | phenyl |
| 4-pentoxybenzoyl | " | phenyl |
| 2-chlorobenzoyl | " | phenyl |
| 3-bromobenzoyl | " | phenyl |
| 2-cyanobenzoyl | (side chain with OSi(CH₃)₃) | phenyl |
| acetyl | " | phenyl |
| proprionyl | " | phenyl |
| butyryl | " | phenyl |
| pentanoyl | " | phenyl |
| benzoyl | " | phenyl |
| 2-methylbenzoyl | " | phenyl |
| 3-ethylbenzoyl | " | phenyl |
| 4-pentylbenzoyl | " | phenyl |
| 4-isopropylbenzoyl | " | phenyl |
| 2-methoxybenzoyl | " | phenyl |
| 3-propoxybenzoyl | " | phenyl |
| 4-pentoxybenzoyl | " | phenyl |
| 2-chlorobenzoyl | " | phenyl |
| 3-bromobenzoyl | " | phenyl |
| 3-fluorobenzoyl | " | phenyl |
| 4-iodobenzoyl | " | phenyl |
| 2-nitrobenzoyl | " | phenyl |
| 2-cyanobenzoyl | " | phenyl |
| benzoyl | (side chain with OC(O)(CH₂)₃CH₃) | phenyl |
| benzoyl | (side chain with OC(O)C₆C₅) | phenyl |
| benzoyl | (side chain with OSi(CH₃)₃) | phenyl |
| benzoyl | (side chain with OC(O)C₆H₅) | phenyl |
| benzoyl | (side chain with OH) | phenyl |

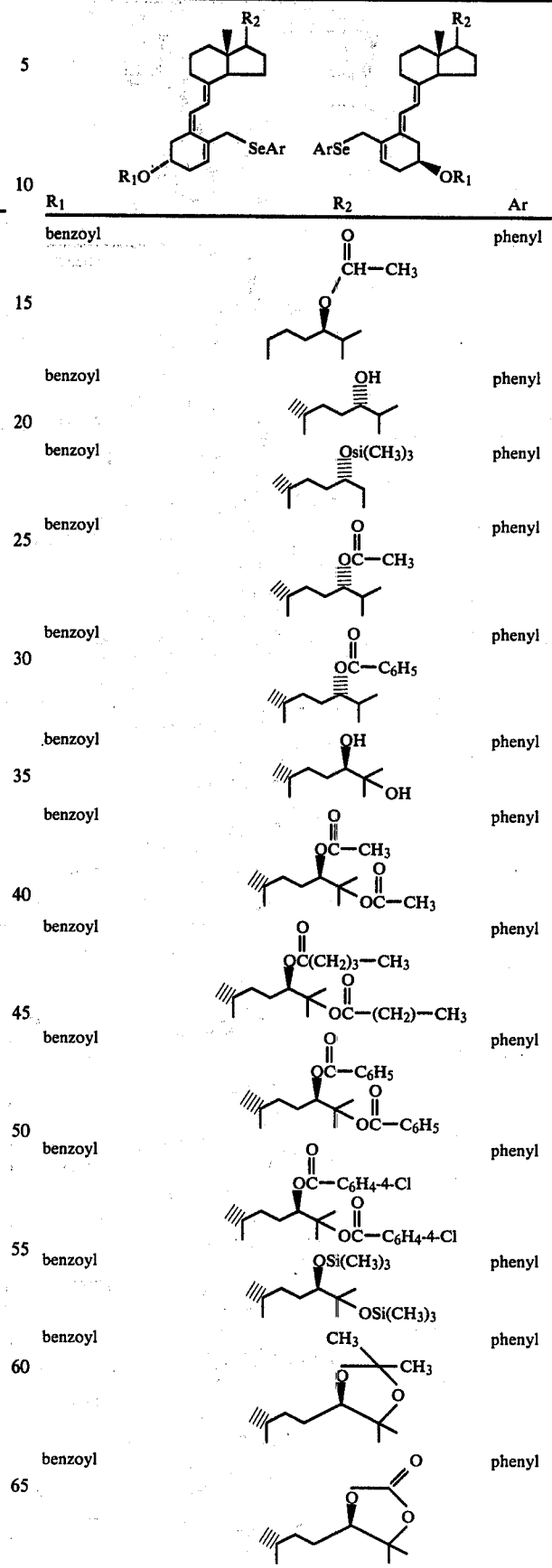

| R₁ | R₂ | Ar |
|---|---|---|
| benzoyl | (side chain with OCH(O)CH₃) | phenyl |
| benzoyl | (side chain with OH) | phenyl |
| benzoyl | (side chain with OSi(CH₃)₃) | phenyl |
| benzoyl | (side chain with OC(O)CH₃) | phenyl |
| benzoyl | (side chain with OC(O)C₆H₅) | phenyl |
| benzoyl | (side chain with OH, OH diol) | phenyl |
| benzoyl | (side chain with two OC(O)CH₃) | phenyl |
| benzoyl | (side chain with OC(O)(CH₂)₃—CH₃ and OC(O)—(CH₂)—CH₃) | phenyl |
| benzoyl | (side chain with two OC(O)—C₆H₅) | phenyl |
| benzoyl | (side chain with two OC(O)—C₆H₄-4-Cl) | phenyl |
| benzoyl | (side chain with two OSi(CH₃)₃) | phenyl |
| benzoyl | (side chain with acetonide CH₃/CH₃) | phenyl |
| benzoyl | (side chain with cyclic carbonate) | phenyl |

Table I-continued

| R₁ | R₂ | Ar |
|---|---|---|
| benzoyl | 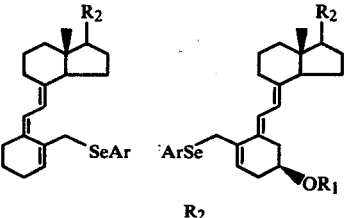 | phenyl |
| benzoyl | 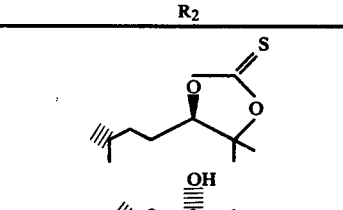 | phenyl |
| benzoyl | 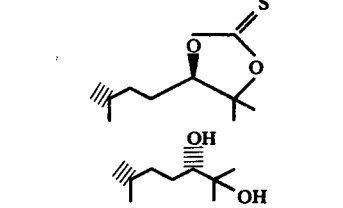 | phenyl |
| benzoyl | 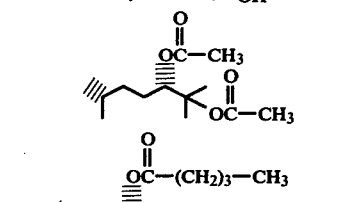 | phenyl |
| benzoyl | 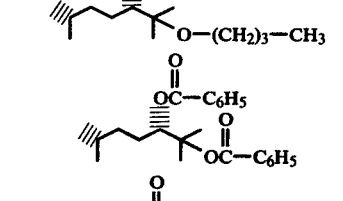 | phenyl |
| benzoyl | 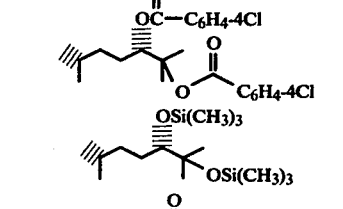 | phenyl |
| benzoyl | 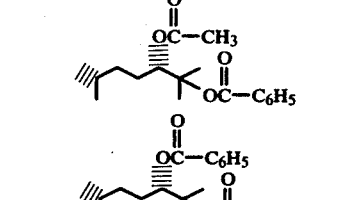 | phenyl |
| benzoyl | 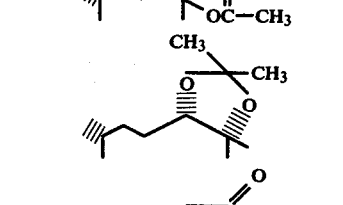 | phenyl |
| benzoyl | 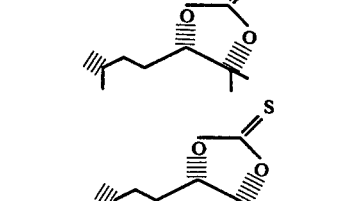 | phenyl |
| benzoyl | 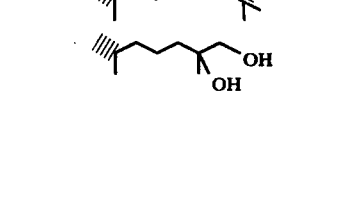 | phenyl |
| benzoyl | 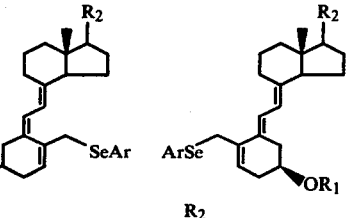 | phenyl |
| benzoyl | 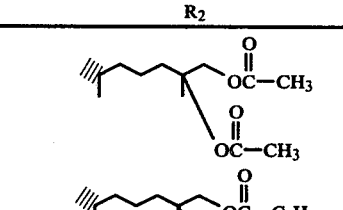 | phenyl |
| benzoyl | 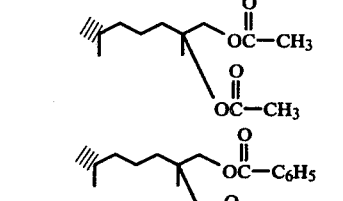 | phenyl |
| benzoyl | 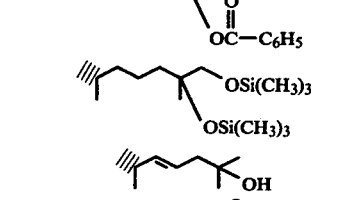 | phenyl |
| benzoyl | 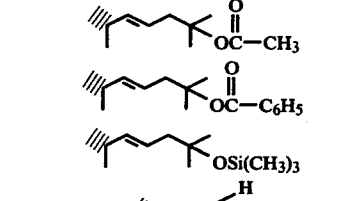 | phenyl |
| benzoyl | 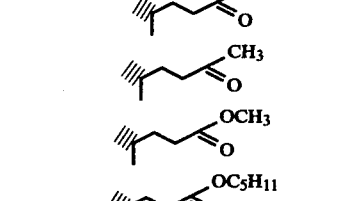 | phenyl |
| benzoyl | 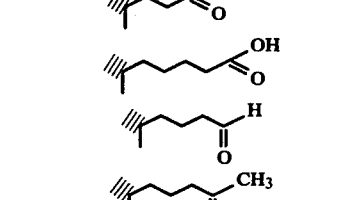 | phenyl |
| benzoyl | 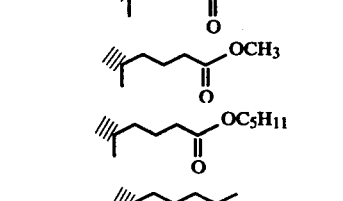 | phenyl |
| benzoyl | 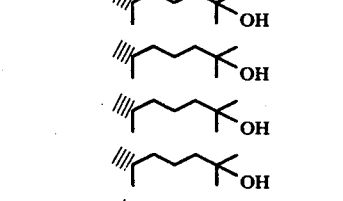 | phenyl |
| benzoyl | 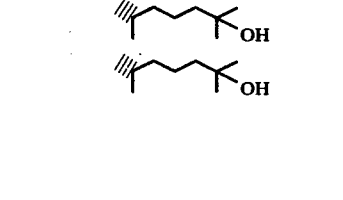 | phenyl |
| benzoyl | 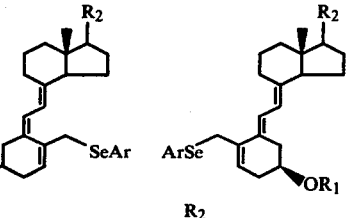 | phenyl |
| benzoyl | 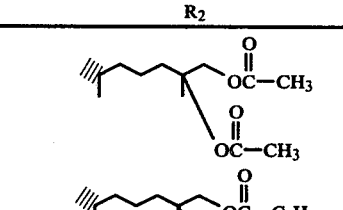 | phenyl |
| benzoyl | 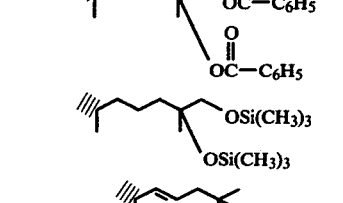 | phenyl |
| benzoyl | 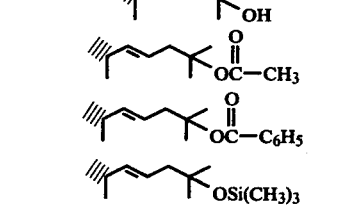 | phenyl |
| benzoyl | 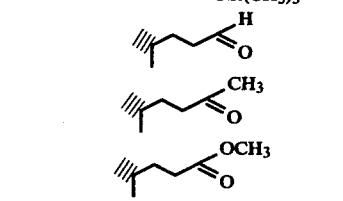 | phenyl |
| benzoyl | 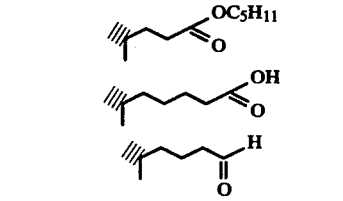 | phenyl |
| benzoyl | 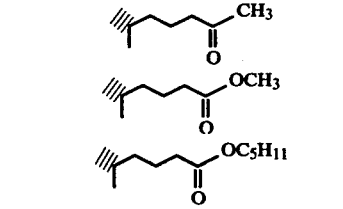 | phenyl |
| benzoyl | 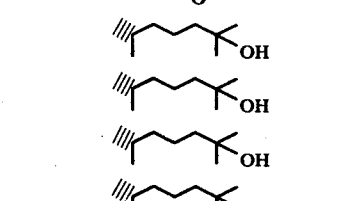 | phenyl |
| benzoyl | 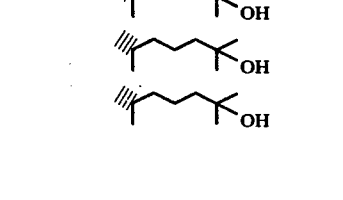 | phenyl |
| benzoyl | 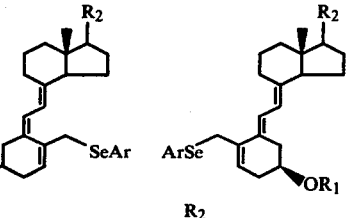 | phenyl |
| 4-chlorophenyl | 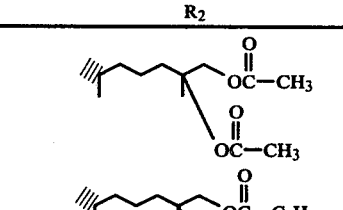 | phenyl |
| 2-methylphenyl | " | phenyl |
| 3-ethoxyphenyl | 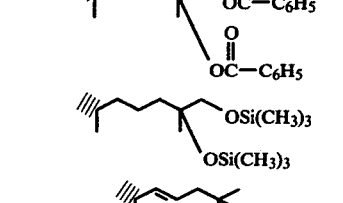 | phenyl |
| 4-nitrophenyl | 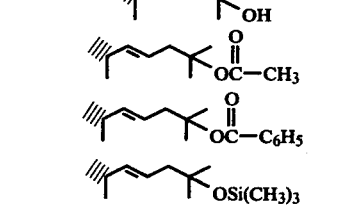 | phenyl |
| 2-bromophenyl | 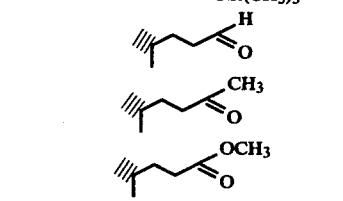 | phenyl |
| trimethylsilyl | 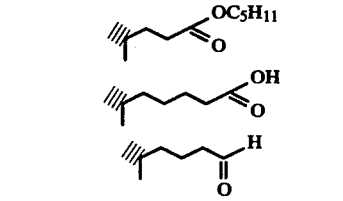 | phenyl |

Table I-continued

| $R_1$ | $R_2$ | Ar |
|---|---|---|
| t-butyldimethylsilyl | ⫽⫽⫽⟨⟩—OH (with side chain) | phenyl |
| phenyldimethylsilyl | ⫽⫽⫽⟨⟩—O-C(=O)-CH$_3$ | phenyl |
| trimethylsilyl | ⫽⫽⫽⟨⟩—O-C(=O)-C$_6$H$_5$ | phenyl |
| trimethylsilyl | ⫽⫽⫽⟨⟩—OSi(CH$_3$)$_3$ | phenyl |

PREPARATION 2

19-Phenylseleneno 9,10-secocholesta-1(10) 5E, 7E-triene-3β-ol, 3-benzoate

To a solution of cholecalciferol benzoate (250 mg) in chloroform (5 ml) is added phenylseleninic anhydride (250 mg) and lithium chloride (20 mg) and heated at 55° for 20 minutes. The solution is poured into water and the mixture extracted with more chloroform. The extracts are washed with a sodium bicarbonate solution and then brine. After drying, the solution is evaporated to yield a residue which is chromatographed on silica gel (10% water), eluting with hexane/ethylacetate mixture, to yield 19-phenylseleno 9,10-secocholesta-1(10) 5E, 7E-triene-3β-ol, 3 benzoate.

PREPARATION 3

19-Phenylseleneno-9,10 secocholesta-1(10)5E, 7E triene-3β-25 diol, 3,25-bis-trimethyl silyl ether To a solution of 25-hydroxy cholecalciferol-bis-trimethylsilyl ether (100 mg), prepared in conventional manner from the diol and pyridine/chlorotrimethyl silane, in dry tetrahydrofuran at −78° C., is added dropwise during a period of 5 minutes to a solution of phenylselenenylchloride (74 mg) in tetrahydrofuran (1 ml). After 20 minutes, 1,5-diazabicyclo[4.5.0]undec-5-ene (0.3 ml) is added, and the solution warmed to room temperature. The mixture is poured into water and extracted with hexane. The extracts are washed successively with brine, dilute hydrochloric acid, brine, a sodium bicarbonate solution and then dried over sodium sulfate. The residue, after evaporation, is chromatographed over silica gel, eluting with hexane containing ½% ethyl acetate to yield the crude 19-phenylseleno-9,10 secocholesta-1(10)(5E), 7E-triene-3β-25 diol, 3,25 bis-trimethyl silylether as an oil.

NMR (CDCl$_3$) SO.135 (18H); 0.58s (3H); 1.20s(6H); 3.55s (24); 3.55m (1H); 5.33m (1H); 5.92 and 6.53 AB, J=12 Hz, (2H); F.10–7.60m (5H).

PREPARATION 4

19-Phenylseleneno-9,10-secocholesta-1(10), 5E, 7E-triene-3β,25-diol, 3-benzoate, 25-trimethyl silylether (i) To a solution of 25-hydroxycholecalciferol (5.0 g.) in pyridine (25 ml.) at −15°, under an atmosphere of argon, is added 4-(N,N-dimethylamino)-pyridine (50 mg) followed by benzoyl chloride (2.10 ml.). The solution is warmed to 0° and kept at this temperature for 1.5 hours. After cooling to −15°, trimethylchlorosilane (1.75 ml.) is added and then the mixture is heated to room temperature for 10 minutes, before pouring into water. The mixture is extracted with hexane (500 ml.) and the extracts washed with brine, dilute hydrochloric acid, brine, sodium bicarbonate solution, brine and then dried over sodium sulfate. Evaporation of the solution yields 25-hydroxycholecalciferol, 3-benzoate, trimethylsilylether as an oil.

(ii) The 25-hydroxycholecalciferol, 3-benzoate, trimethylsilylether obtained in (i) is dissolved in hexamethyl phosphoric triamide (25 ml.) under an atmosphere of argon and N-phenylselenenosuccinimide (9.0 g.) is added, and the solution then heated to 72° for 3.5 hours before pouring into water and extracting with a mixture of methylene chloride (100 ml.) and hexane (200 ml.). The extract is washed successively with water (3 times), sodium bicarbonate solution and finally with water. After drying over sodium sulfate the solution is evaporated to an oil, chromatographed on silica gel (10% water) eluting with ethyl acetate/hexane. The product is then crystallized from iso-propanol to give 19-phenylseleno-9,10-secocholesta-1(10), 5Z, 7E-triene-3β,25-diol, 3-benzoate, 25-trimethylsilylether: 0.6 (5% ethylacetate in Skellysolve B).

[α]$_D$ (CHCl$_3$, C=0.8635) +164°.

NMR (CDCl$_3$): δ0.1s (9H); 0.53s (3H); 0.93d, J=6 Hz (3H); 1.20s (6H); 3.80s (2H); 5.27m (1H); 5.53t, J=3 Hz (1H); AB at 5.93 and 6.67, J=11 Hz (2H); 7.17–7.67 complex (8H); 7.80–8.17 complex (2 H).

PREPARATION 4a

Trimethylsilylation of 19-phenylseleneno-9,10-secocholesta-1(10),5E,7E-triene-3β, 25-diol, 3-benzoate Trimethylchlorosilane (0.10 ml.) is added to a solution of 19-phenylseleneno-9,10-secocholesta-1(10),5E,7E-triene-3β,25-diol, 3-benzoate (330 mg.) in pyridine (2 ml.) containing 4-(N,N-dimethylamino)pyridine (10 mg.) at −15°. After stirring at room temperature for 0.5 hour the mixture is poured into water and extracted with hexane (150 ml.). The extract is washed with dilute hydrochloric acid, brine, sodium bicarbonate solution, and then brine. After drying over sodium sulfate the solvent is removed and the residue crystallized from isopropanol to give 19-phenylseleneno-9,10-secocholesta-1(10),5E,7E-triene-3β,25-diol, 3-benzoate, 25-trimethylsilylether.

PREPARATION 5

19-Phenylseleneno-9,10-secocholesta-1(10),5E,7E-triene-3β,25-diol, 3-benzoate A solution of N-phenylselenenosuccinimide (9.0 g.) and 25-hydroxycholecalciferol-3-benzoate (6.5 g.) is heated at 72° for 4.5 hours and then poured into water. The mixture is extracted with a 30% solution of methylene chloride in hexane (500 ml.) and the extracts washed twice with water, sodium bicarbonate solution, water and then dried over sodium sulfate. After removal of solvent the residue is chromatographed on silica gel (10% water) eluting with ethyl acetate/hexane (gradient-wise to ca. 7% ethylacetate. The product is crystallized from isopropanol to give 19-phenyl-seleneno-9,10-secocholesta-1(10),5E,7E-triene-3β,25β- diol, 3-benzoate (2.2 g., 222). Rf: 0.6 (two passes in 20% ethylacetate/Skellysolve B; m.p. 107°-108° C.

$[\alpha]_D$ (CHCl$_3$, C=0.7635)+187°.

NMR (CDCl$_3$): δ0.52s (3H); 0.93d, J=6 Hz (3H); 1.20s (6H); 5.23m (1H); 5.53t, J=3 Hz (1H); AB at 5.60 and 6.60, J=11 Hz (2H); 7.17-7.63 complex (8H); 7.93-8.10 complex (2H).

EXAMPLE 1

(i) 9,10-Secocholesta-5Z,7E,10(19)-triene-1α,3β-diol, 3 benzoate (ii) 9,10-Secocholesta-5E,7E,10(19)-triene-1β,3β-diol, 3-benzoate (iii) 9,10-Secocholesta-5E,7E,10(19)-triene-1α,3β-diol, 3-benzoate To a stirred solution of 19-phenylseleneno 9,10-secocholesta-1(10),5Z,7E-triene-3β-ol, 3-benzoate (1.93 g) in dry tetrahydrofuran (20 ml.) containing diisopropylethylamine (0.05 ml) at −16° C. is added 90% hydrogen peroxide (0.25 ml.). The mixture is allowed to warm slowly and at ca −5° C. an exotherm to ca +10° occured. The mixture is poured into water and extracted with ethyl acetate. The extracts are washed with dilute hydrochloric acid, brine, sodium bicarbonate solution and then brine. The extracts are dried over sodium sulfate and then evaporated to a residue which was chromatographed on silica gel (10% water) eluting with hexane/ethylacetate mixture. Three compounds are isolated. They are in order of elution.

(i) 9,10-Secocholesta-5Z,7E,10(19)-triene-1α,3β-diol, 3-benzoate.

NMR (CDCl$_3$): δ0.55s (3H); 4.48m (1H); 5.07s(1H); 5.40s (1H); 5.47m (1H); 6.05 and 6.38 AB, J=11.0 Hz, (2H); 7.27-7.60m (3H); 7.90-8.10m (2H).

Hydrolysis of this material with aqueous methanolic potassium hydroxide yielded crystalline 1α-hydroxycholecalciferol, identical to authentic material.

(ii) 9,10-Secocholesta-5E,7E,10(19)-triene-1β,3β-diol, 3-benzoate.

NMR (CDCl$_3$): δ0.47s (3H); 4.22m(1H); 5.08s (1H); 5.13s(1H); 5.13m(1H); 5.83 and 6.63 AB, J=12H$_3$, (2H); 7.27-7.60m (3H); 7.90-8.10m (2H).

(iii) 9,10-Secocholesta-5E,7E,10(19)-triene-1α,3β-diol-3-benzoate.

NMR (CDCl$_3$): 0.40s (3H); 4.57t, J=5 Hz, (1H); 5.03 s (1H); 5.15s (1H); 5.50m (1H); 5.82 and 6.62 AB, J=12 Hz, (2H); 7.27-7.60m (3H); 7.90-8.10m (2H).

Utilizing procedures similar to those described in Example 1, but substituting the appropriate seleneno compounds for 19-phenylseleno-9,10-secocholesta-1(10),5Z,7E-triene-3β-ol, 3-benzoate there is obtained the following compounds

TABLE II

| R$_1$ | R$_2$ | Ar |
|---|---|---|
| benzoyl | ⫽⟨(CH$_2$)$_3$CH(CH$_3$)$_2$⟩ | phenyl |

TABLE II-continued

| R$_1$ | R$_2$ | Ar |
|---|---|---|
| 2-methylbenzoyl | " | phenyl |
| 3-t-butylbenzoyl | " | phenyl |
| 4-pentylbenzoyl | " | phenyl |
| 2-methoxybenzoyl | " | phenyl |
| 4-pentoxybenzoyl | " | phenyl |
| 2-chlorobenzoyl | " | phenyl |
| 3-bromobenzoyl | " | phenyl |
| 3-fluorobenzoyl | " | phenyl |
| 4-iodobenzoyl | " | phenyl |
| 4-nitrobenzoyl | " | phenyl |
| 2-cyanobenzoyl | " | phenyl |
| acetyl | ⫽⟨R with OH⟩ | phenyl |
| propionyl | " | phenyl |
| butyryl | " | phenyl |
| pentanoyl | " | phenyl |
| benzoyl | " | phenyl |
| 2-methylbenzoyl | " | phenyl |
| 3-ethylbenzoyl | " | phenyl |
| 4-pentylbenzoyl | " | phenyl |
| 4-isopropylbenzoyl | " | phenyl |
| 2-methoxybenzoyl | " | phenyl |
| 3-propoxybenzoyl | " | phenyl |
| 4-pentoxybenzoyl | " | phenyl |
| 2-chlorobenzoyl | " | phenyl |
| 3-bromobenzoyl | " | phenyl |
| 2-cyanobenzoyl | ⫽⟨R with OC(O)—CH$_3$⟩ | phenyl |
| acetyl | " | phenyl |
| proprionyl | " | phenyl |
| butyryl | " | phenyl |
| pentanoyl | " | phenyl |
| benzoyl | " | phenyl |
| 2-methbenzoyl | " | phenyl |
| 3-ethylbenzoyl | " | phenyl |
| 4-pentylbenzoyl | " | phenyl |
| 4-isopropylbenzoyl | " | phenyl |
| 2-methoxybenzyoyl | " | phenyl |
| 3-propoxybenzoyl | " | phenyl |
| 4-pentoxybenzoyl | " | phenyl |
| 2-chlorobenzoyl | " | phenyl |
| 3-bromobenzoyl | " | phenyl |
| 2-cyanobenzoyl | ⫽⟨R with OSi(CH$_3$)$_3$⟩ | phenyl |
| acetyl | " | phenyl |
| proprionyl | " | phenyl |
| butyryl | " | phenyl |
| pentanoyl | " | phenyl |
| benzoyl | " | phenyl |
| 2-methylbenzoyl | " | phenyl |
| 3-ethylbenzoyl | " | phenyl |
| 4-pentylbenzoyl | " | phenyl |
| 4-isopropylbenzoyl | " | phenyl |
| 2-methoxybenzoyl | " | phenyl |
| 3-propoxybenzoyl | " | phenyl |
| 4-pentoxybenzoyl | " | phenyl |
| 2-chlorobenzoyl | " | phenyl |
| 3-bromobenzoyl | " | phenyl |
| 3-fluorobenzoyl | " | phenyl |
| 4-iodobenzoyl | " | phenyl |
| 2-nitrobenzoyl | " | phenyl |
| 2-cyanobenzoyl | " | phenyl |
| benzoyl | ⫽⟨R with OC(O)—(CH$_2$)$_3$—CH$_3$⟩ | phenyl |

TABLE II-continued

| $R_1$ | $R_2$ | Ar |
|---|---|---|
| benzoyl | (chain with C≡C, OC(=O)-C$_6$C$_5$) | phenyl |
| benzoyl | (chain with OSi(CH$_3$)$_3$) | phenyl |
| benzoyl | (chain with OC(=O)-C$_6$H$_5$) | phenyl |
| benzoyl | (chain with OH) | phenyl |
| benzoyl | (chain with OC(=O)CH$_3$) | phenyl |
| benzoyl | (chain with OH) | phenyl |
| benzoyl | (chain with OSi(CH$_3$)$_3$) | phenyl |
| benzoyl | (chain with OC(=O)CH$_3$) | phenyl |
| benzoyl | (chain with OC(=O)C$_6$H$_5$) | phenyl |
| benzoyl | (chain with OH, OH diol) | phenyl |
| benzoyl | (chain with OC(=O)CH$_3$ and OC(=O)CH$_3$) | phenyl |
| benzoyl | (chain with OC(=O)(CH$_2$)$_3$CH$_3$ and OC(=O)(CH$_2$)$_3$CH$_3$) | phenyl |
| benzoyl | (chain with OC(=O)C$_6$H$_5$ and OC(=O)C$_6$H$_5$) | phenyl |
| benzoyl | (chain with OC(=O)-C$_6$H$_4$-4-Cl and OC(=O)-C$_6$H$_4$-4-Cl) | phenyl |
| benzoyl | (chain with OSi(CH$_3$)$_3$ and OSi(CH$_3$)$_3$) | phenyl |
| benzoyl | (chain with dioxolane CH$_3$, CH$_3$) | phenyl |
| benzoyl | (chain with cyclic carbonate O-C(=O)-O) | phenyl |
| benzoyl | (chain with cyclic thiocarbonate O-C(=S)-O) | phenyl |
| benzoyl | (chain with OH, OH) | phenyl |
| benzoyl | (chain with OC(=O)CH$_3$ and OC(=O)CH$_3$) | phenyl |
| benzoyl | (chain with OC(=O)(CH$_2$)$_3$CH$_3$ and O-(CH$_2$)$_3$-CH$_3$) | phenyl |
| benzoyl | (chain with OC(=O)C$_6$H$_5$ and OC(=O)C$_6$H$_5$) | phenyl |
| benzoyl | (chain with OC(=O)-C$_6$H$_4$-4Cl and OC(=O)-C$_6$H$_4$-4Cl) | phenyl |
| benzoyl | (chain with OSi(CH$_3$)$_3$ and OSi(CH$_3$)$_3$) | phenyl |
| benzoyl | (chain with OC(=O)CH$_3$ and OC(=O)-C$_6$H$_5$) | phenyl |

TABLE II-continued

Structures VI and VII (steroid skeletons with HO and OR₁ groups, Ar substituent)

| R₁ | R₂ | Ar |
|---|---|---|
| benzoyl | -C(OC-C₆H₅)(OC-CH₃) (diacyloxy branched) | phenyl |
| benzoyl | -C(CH₃)₂-O-O- (dioxy cyclic with CH₃, CH₃) | phenyl |
| benzoyl | cyclic carbonate (O-C(=O)-O) | phenyl |
| benzoyl | cyclic thiocarbonate (O-C(=S)-O) | phenyl |
| benzoyl | -CH(OH)-...OH | phenyl |
| benzoyl | -C(OC(=O)CH₃)(OC(=O)CH₃) | phenyl |
| benzoyl | -C(OC(=O)C₆H₅)(OC(=O)C₆H₅) | phenyl |
| benzoyl | -C(OSi(CH₃)₃)(OSi(CH₃)₃) | phenyl |
| benzoyl | -CH=CH-C(CH₃)₂-OH | phenyl |
| benzoyl | -CH=CH-C(CH₃)₂-OC(=O)CH₃ | phenyl |
| benzoyl | -CH=CH-C(CH₃)₂-OC(=O)C₆H₅ | phenyl |
| benzoyl | -CH=CH-C(CH₃)₂-OSi(CH₃)₃ | phenyl |
| benzoyl | -CH₂-C(=O)H | phenyl |
| benzoyl | -CH₂-C(=O)CH₃ | phenyl |
| benzoyl | -CH₂-C(=O)OCH₃ | phenyl |
| benzoyl | -CH₂-C(=O)OC₅H₁₁ | phenyl |
| benzoyl | -CH₂-CH₂-C(=O)OH | phenyl |
| benzoyl | -CH₂-CH₂-C(=O)H | phenyl |
| benzoyl | -CH₂-CH₂-C(=O)CH₃ | phenyl |
| benzoyl | -CH₂-CH₂-C(=O)OCH₃ | phenyl |
| benzoyl | -CH₂-CH₂-C(=O)OC₅H₁₁ | phenyl |
| 4-chlorophenyl | -C(CH₃)₂-OH | phenyl |
| 2-methylphenyl | -C(CH₃)₂-OH | phenyl |
| 3-ethoxyphenyl | -C(CH₃)₂-OH | phenyl |
| 4-nitrophenyl | -C(CH₃)₂-OH | phenyl |
| 2-bromophenyl | -C(CH₃)₂-OH | phenyl |
| trimethylsilyl | -C(CH₃)₂-OH | phenyl |
| t-butyldimethylsilyl | -C(CH₃)₂-OH | phenyl |
| phenyldimethylsilyl | -C(CH₃)₂-OC(=O)CH₃ | phenyl |
| trimethylsilyl | -C(CH₃)₂-OC(=O)C₆H₅ | phenyl |
| trimethylsilyl | -C(CH₃)₂-OSi(CH₃)₃ | phenyl |

EXAMPLE 2

9,10-Secocholesta-5E,7E,10(19)-triene-1α,3β,25-triol-3.25-bis-trimethylsilylether In a manner similar to that described in Example 1(iii), 19-phenylseleneno-9,10-secocholesta-1(10),5E,7E-triene-3β,25-diol, 3,25-bistrimethylsilylether is oxidized to yield 9,10-secocholesta-5E,-7E,10(19)-triene-1α3,β,25-triol-3,25-bistrimethylsilylether.

NMR (CDCl₃): δ0.15s (9H); 0.20s (9H); 0.61s (3H); 125s (6H); 4.20m (1H); 4.50m (1H); 4.98s (1H); 5.11s (1H); 5.88 and 6.58 AB, J=12 Hz, (2H).

Hydrolysis with dilute hydrochloric yielded crystalline 9,10, secocholesta-5E,7E,10(19)-triene-1α,3β,25-triol.

NMR (CDCl₃): δ0.59s (3H); 0.72s (6H); 4.19m (1H); 4.49m (1H); 4.87s (1H); 5.12s (1H); 5.87 and 6.57AB, J=12 H₂, (2H).

Utilizing the procedure similar to that used in Example 2, but substituting the 3,25-substituted phenyl-seleneno compounds described in Preparation 1 for 19-phenyl seleneno-9,10-secocholesta-1(10),5E,7E-triene-3β,25-diol, 3,25-bistrimethylsilylether there is obtained the corresponding 9,10-secocholesta-5E,7E,10(19)-triene-1α,3β,25-triol, 3,25-derivative.

EXAMPLE 3

9,10-Secocholesta-5Z,7E,10(19)-triene-1α,3β-diol, 3-benzoate 9,10-Secocholesta-5E,7E,10(19)-triene-1α,3β-diol, 3-benzoate (100 mg.) is dissolved in hexane (20 ml.) in a pyrex photo reaction tube and the solution vigorously deoxygenated, the atmosphere above the solution being replaced by argon. The solution is irradiated with 253.7 n.m. lamps for three hours. The solution is then placed directly on a silica gel (10% water) chromatographic column and the product 9,10-secocholesta-5Z,7E,10(19)-triene-1α,3β-diol, 3-benzoate separated from the residual starting material.

The product has:
NMR (CDCl$_3$): 0.55s (3H); 4.48m (1H); 5.07s (1H); 5.40s (1H); 5.47m (1H); 6.05 and 6.38, AB, J=11.0 Hz, (2H); 7.27–7.60m (3H); 7.90–8.10m (2H).

This material is identical to the product (i) in Example 1. Hydrolysis of this material with aqueous methanolic potassium hydroxide yields 9,10-secocholesta-5Z,7E,10(19)-triene 1α,3β-diol that is identical with an authentic sample.

EXAMPLE 4

9,10-Secocholesta-5Z,7E,10(19)-triene-1α,3β,25-triol, 3,25-Bis-trimethylsilylether In a like fashion to that described in Example 3, 9,10-secocholesta-5E,7E,10(19)-triene-1α,3β,25-triol-3,25-bis-trimethylsilyl derivative is irradiated to yield 9,10-secocholesta-5Z,7E,10(19)-triene-1α,3β,25-triol, 3,25-bis-trimethylsilyl derivative.

NMR (CDCl$_3$): δ0.16s (9H); 0.20s (9H); 0.61s(3H); 1.25s (6H); 4.23m (1H); 4.45m (1H); 5.00s (1H); 5.30s (1H); 6.03 and 6.40 AB, J=11.5 Hz, (2H).

Mild hydrolysis with cold dilute hydrochloric acid yields 9,10-secocholesta-5Z,7E,10(19)-triene-1α,3β,25-triol identical to an authentic specimen.

EXAMPLE 5

9,10-Secocholesta-5Z,7E,10(19)-triene-1β, 3β-diol, 3-benzoate

In a similar fashion to that described in Example 3, 9,10-secocholesta-5E,7E,10(19)-triene-1β,3β-diol-3-benzoate is irradiated to yield 9,10-secocholesta-5Z,7E,10(19)-triene-1β,3β-diol, 3-benzoate.

NMR (CDCl$_3$): δ0.52s (3H); 4.20m (1H); 5.03s (1H); 5.17m (1H); 5.40m (1H); 6.00 and 6.42 AB, J=11.05, (2H); 7.27–7.60 m (3H); 7.90–8.10m (2H).

Hydrolysis of this material with aqueous methanolic potassium hydroxide yields 9,10-secocholesta-5Z,7E,10(19)-triene-1β,3β,diol.

NMR (CDCl$_3$): δ0.53s (3H); 4.07m (1H); 4.33m (1H); 4.98 (1H); 5.27s (1H); 6.05 and 6.43 AB, J=10.5 Hz, (2H).

EXAMPLE 6

Oxidation of 19-phenylseleneno-9,10-secocholesta-1(10),5E,7E-triene-3β-25-diol, 3-benzoate,25-trimethylsilylether To a solution of 19-phenylseleneno-9,10-secocholesta-1(10),5Z,7E-triene-3β,25-diol, 3-benzoate, 25-trimethylsilylether (2.40 g.) in dry tetrahydrofuran (25 ml.) containing diiso-propylethylamine (0.05 ml.) under argon at −15° is added dropwise a solution of diphenyldiselenide (50 mg.) and diisopropylethylamine (0.05 ml.) in dry tetrahydrofuran (5 ml.) that has been heated with hydrogen peroxide (0.20 ml., 90%) at 50° until it is clear and colorless. The solution is allowed to warm slowly to −10° at which temperature a pronounced exotherm is observed. The mixture is poured into cold water and extracted with methylene chloride (500 ml.). The extract is washed with cold dilute hydrochloric acid, cold brine, cold sodium bicarbonate solution, cold brine and then dried over sodium sulfate. The solvent is removed and the oily residue chromatographed over silica gel (10% water) eluting with ethyl acetate/Skellysolve B gradient wise. The products elutes at ca. 8–9% ethyl acetate. The first material eluted is 9,10-secocholesta-5E,7E,10(19)-triene-1β,3β, 25-triol, 3-benzoate, 25-trimethylsilylether.

Rf: 0.45 (20% ethylacetate/Skellysolve B).

The second material eluted is 9,10-secocholesta-5E,7E,10(19)-triene-1α,3β,25-triol, 3-benzoate, 25-trimethylsilylether.

NMR (CDCl$_3$): δ0.1s (9H); 0.40s (3H); 0.90d, J=6 Hz (3H); 5.03s (1H); 5.13 (1H); 5.50m (1H); AB at 5.80 and 6.60, J=11 Hz (2H); 7.17–7.60 complex (3H); 7.90–8.10 complex (2H).

EXAMPLE 7

9,10-Secocholesta-5Z,7E,10(19)-triene-1α,3β,25-triol, 3-benzoate, 25-trimethylsilylether 9,10-Secocholesta-5E,7E,10(19)-triene-1α,3β-25-triol, 3-benzoate, 25-trimethylsilylether (52 mg.). is dissolved in dry tetrahydrofuran (20 ml.) in a pyrex photoreaction tube, and the solution rigorously deoxygenated. The atmosphere above the solution is replaced with argon. The solution is irradiated with 253.7 n.m. lamps for four hours. The solvent is removed and the residue chromatographed on silica gel (10% water) eluting with ethyl acetate/hexane. The product, 9,10-secocholesta-5Z,7E,10(19)-triene-1α,3β-25-triol, 3-benzoate, 25-trimethylsilylether (52 mg.), is eluted first, followed by residual starting material (both being eluted with ca. 8–9% ethylacetate). The product has NMR (CDCl$_3$): δ0.1s (9H); 0.6s (3H); 0.93d, J=6 Hz (3H); 1.20s (6H); 4.50M (1H); 5.07s (1H); 5.40s (1H); 5.47 m (1H); AB at 6.05 and 6.38, J=11 Hz (2H); 7.17–7.60 complex (3H); 7.90–8.10 complex (2H).

EXAMPLE 3

1α-25-Dihydroxycholecalciferol

To a solution of 9,10-secocholesta-5Z,7E,10(19)-triene-1α,3β,25-triol, 3-benzoate, 25-trimethylsilylether (350 mg.) in tetrahydrofuran (2 ml.) and methanol (2 ml.) is added dilute hydrochloric acid (0.5 ml., 0.5 N). After 1 minute this is followed by a solution of sodium hydroxide (0.1 ml., 50%). The mixture is heated at 45° for 0.5 hour and then poured into brine. The mixture is extracted with a 5% solution of methanol in methylene chloride (150 ml.). The extracts are washed twice with brine and then dried over sodium sulfate. The solvent is removed and the residue crystallized from methylene chloride (3 ml.) to give 1α,25-dihydroxycholecalciferol, identical with an authentic sample benzoate as an oil.

Rf: 0.65 (20% ethyl acetate/Skellysolve B).

EXAMPLE 9

9,10-Secocholesta-5E,7E-10(19)-triene-1β,3β,25-triol, 3-benzoate and
9,10-secocholesta-5E,7E-10(19)-triene-1α,3β,25-triol, 3-benzoate In a manner exactly similar to that described in Example 6, 19-phenylseleneno-9,10-secocholesta-1(11),5E,7E-triene-3β,25-diol, 3-benzoate (2.25 g.) is oxidized to mixture of the 1α- and 1β-hydroxy-trans-vitamin derivatives, which are separated by chromatography on silica gel (10% water) eluting with ethyl acetate/hexane, gradient-wise to ca. 20% ethyl acetate.

The 9,10-secocholesta-5E,7E-10(19)-triene-1β,3β,25-triol, 3-benzoate is eluted first.

Rf=0.4 (40% ethyl acetate/Skellysolve B).

The 9,10-secocholesta-5E,7E,10(19)-triene-1α,3β,25-triol, 3-benzoate is eluted next.

Rf: 0.35 (40% ethyl acetate/Skellysolve B).

NMR (CDCl₃): δ0.40s (3H); 0.90d, J=6 Hz (3H); 1.20s (6H); 4.53t, J=3 Hz (1H); 5.03s (1H); 5.13s (1H); 5.50 m (1H); AB at 5.80 and 6.60, J=11 Hz (2H); 7.17–7.50 complex (3H); 7.90–8.10 complex (2H).

I claim:

1. A process for preparing a compound having the formula

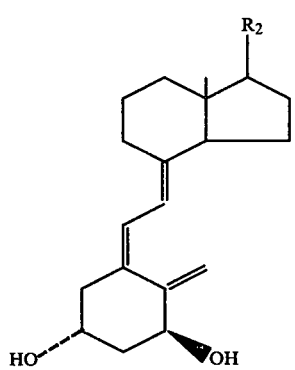

wherein R₂ is selected from the group consisting of

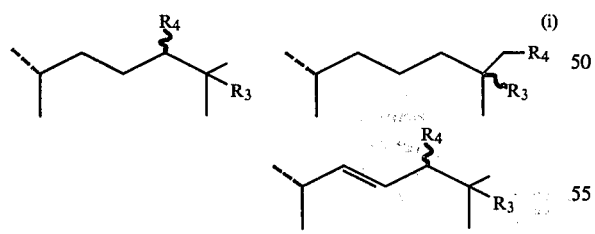

wherein R₃ is selected from the group consisting of hydrogen, hydroxy, trimethylsilyloxy, acyloxy of from 2 to 6 carbon atoms, inclusive, and aroyloxy, wherein aryl is selected from the group consisting of benzoyl and substituted benzoyl; R₄ is selected from the group consisting of hydrogen, hydroxy, trimethylsilyloxy, acyloxy of from 2 to 6 carbon atoms, inclusive and aroyloxy; and wherein R₃ and R₄ when taken together form a group selected from acetonide, carbonate and thiocarbonate; and

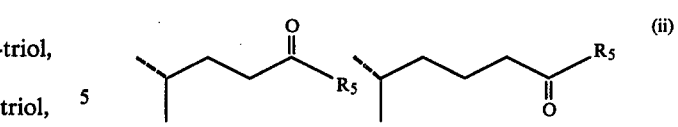

wherein R₅ is selected from the group consisting of hydrogen, hydroxyl and lower alkoxyl of from 1 to 6 carbon atoms, inclusive, which comprises (a) converting a compound selected from the group having the formulae

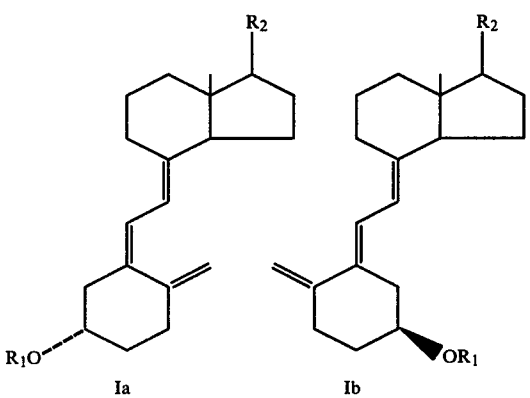

to a compound having the formula

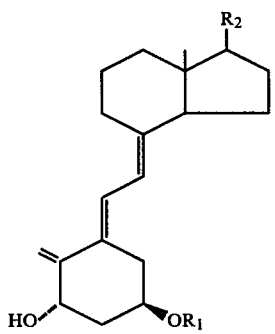

wherein R₁ is selected from the group consisting of hydrogen, trimethylsilyl, t-butyldimethylsilyl, phenyldimethylsilyl, acyl of from 2 to 6 carbon atoms, and aroyl; and (b) converting the compound VI produced in (a) to the compound of formula VIII.

2. A process according to claim 1 wherein step (a) is conducted by reacting compounds having the formulae

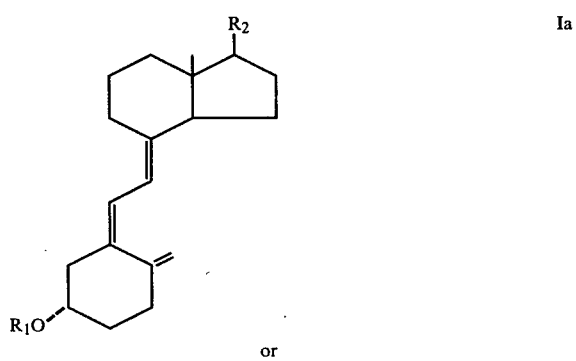

or

-continued

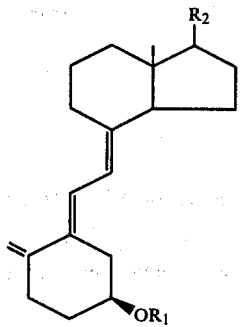
Ib with a selenium reagent selected from the group consisting of aryl selenenyl halide, ArSeX, wherein Ar is phenyl or phenyl substituted with chloro, bromo, lower alkyl, lower alkoxy or nitro, and X is chlorine, bromine, fluorine or iodine, aryl seleninic anhydride,

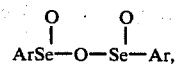

and Ar—Se—$R_6$, wherein $R_6$ is selected from the group consisting of

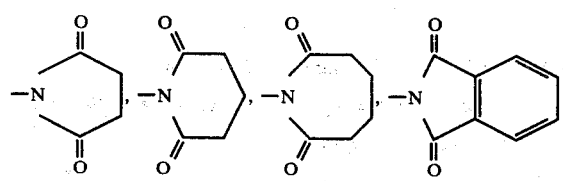

and Ar is the same as defined above, to form a mixture containing compounds having the formulae

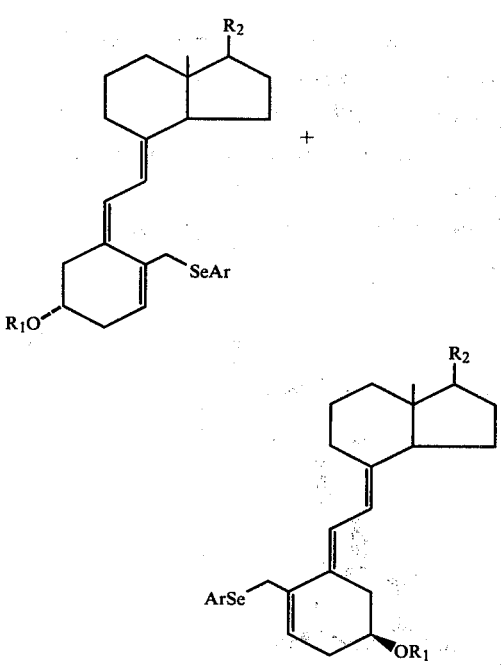

oxidizing the mixture to form a second mixture containing compounds having the formulae

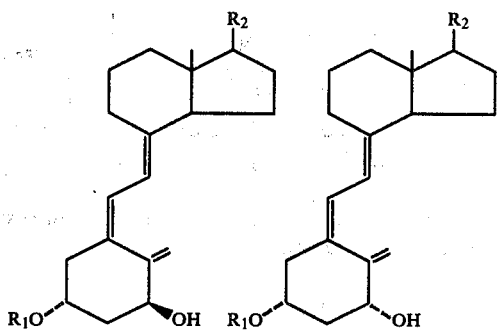

IV    V

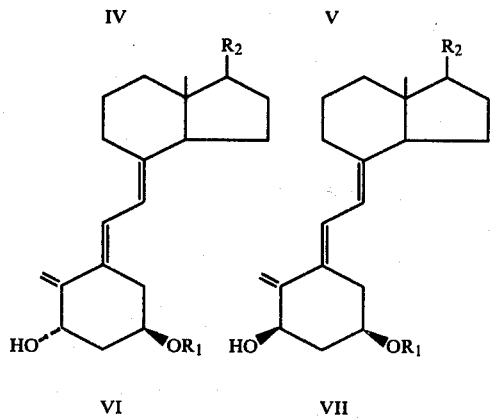

VI    VII and separating the compound of formula VI from the second mixture, wherein $R_1$ and $R_2$ are the same as in claim 1.

3. A process according to claim 1 wherein step (a) is conducted by reacting a compound having the formula

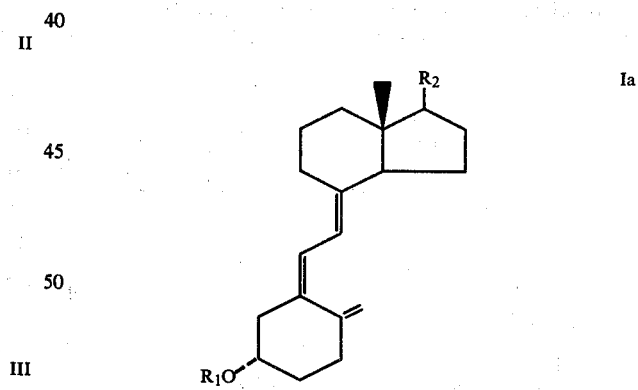
Ia with a selenium reagent selected from the group consisting of aryl selenenyl halide, ArSeX, wherein Ar is phenyl or phenyl substituted with chloro, bromo, lower alkyl, lower alkoxy or nitro, and X is chlorine, bromine, fluorine or iodine, aryl seleninic anhydride,

and Ar—Se—$R_6$, wherein $R_6$ is selected from the group consisting of

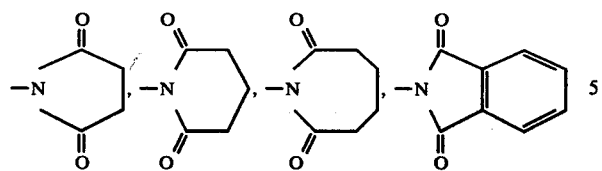

and Ar is the same as defined above, to form a mixture containing compounds having the formulae

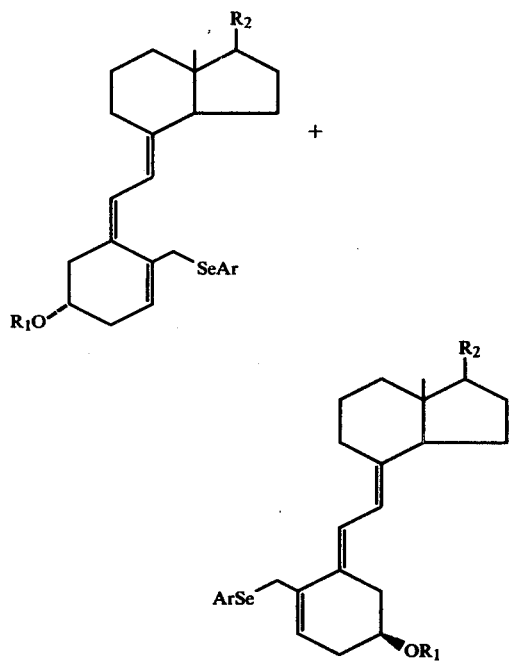

and oxidizing the mixture to form a second mixture containing compounds having the formulae

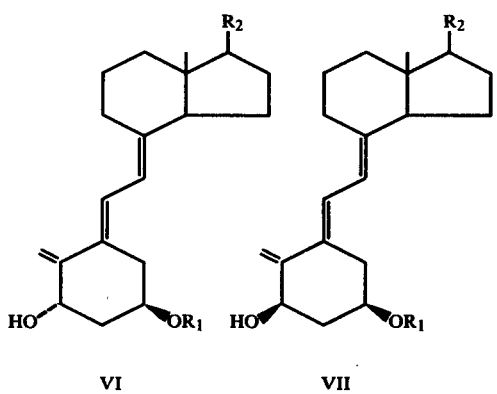

and separating the compound of formula VI from the reaction mixture, wherein $R_1$ and $R_2$ are the same as claim 1.

4. A process according to claim 2 or 3 wherein $R_2$ is selected from the group consisting of

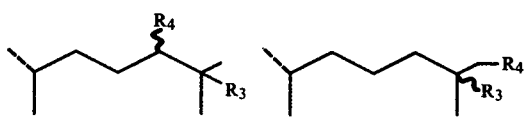

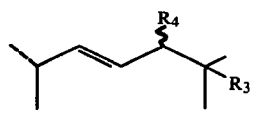

wherein $R_3$ and $R_4$ are the same as in claim 1.

5. A process according to claim 2 or 3 wherein $R_2$ is selected from the group consisting of

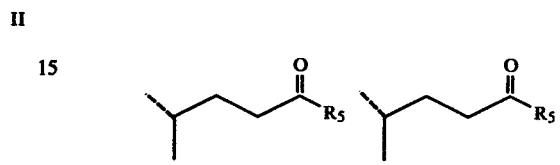

wherein $R_5$ is the same as in claim 1.

6. A process according to claim 4 wherein $R_2$ is

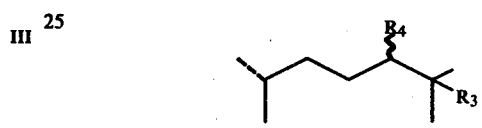

and $R_3$ and $R_4$ are the same as in claim 4.

7. A process according to claim 6 wherein $R_3$ is hydroxy and $R_4$ is hydrogen.

8. A process according to claim 6 wherein $R_3$ is acyloxy and $R_4$ is hydrogen.

9. A process according to claim 8 wherein $R_3$ is acetoxy.

10. A process according to claim 6 wherein $R_3$ is selected from the group consisting of hydrogen and trimethylsilyloxy, and $R_4$ is hydrogen.

11. A process according to claim 10 wherein $R_3$ is trimethylsilyloxy.

12. A process for preparing a compound having the formula

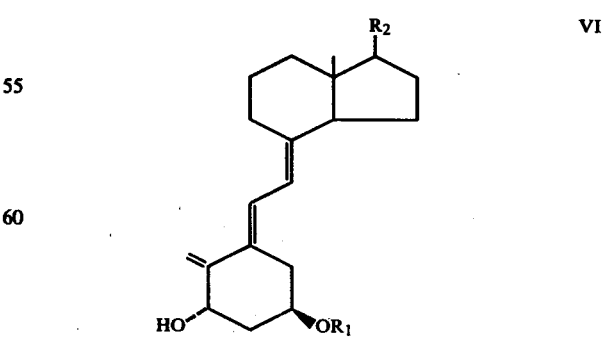

which comprises reacting compounds having the formulae

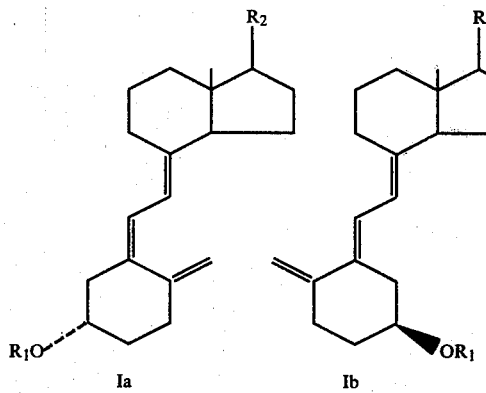

with a selenium reagent selected from the group consisting of aryl selenenyl halide, ArSeX, wherein Ar is phenyl or phenyl substituted with chloro, bromo, lower alkyl, lower alkoxy or nitro, and X is chlorine, bromine, fluorine or iodine, aryl seleninic anhydride,

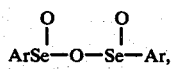

and Ar—Se—$R_6$, wherein $R_6$ is selected from the group consisting of

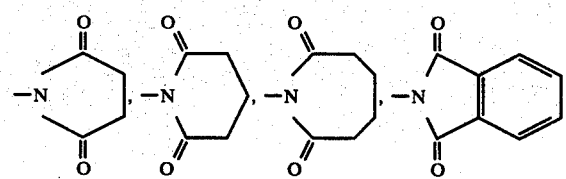

and Ar is the same as defined above, to form a mixture containing compounds having the formulae

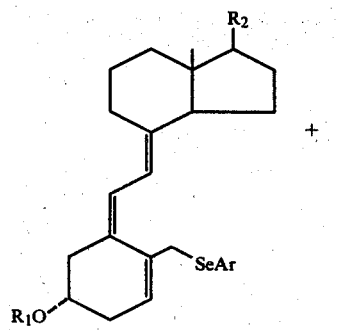

oxidizing the mixture to form a second mixture containing compounds having the formulae

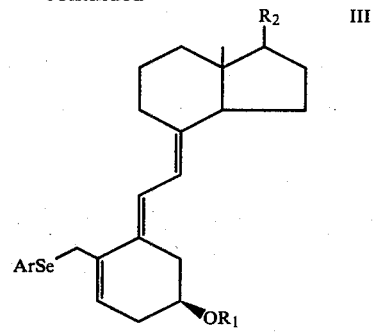

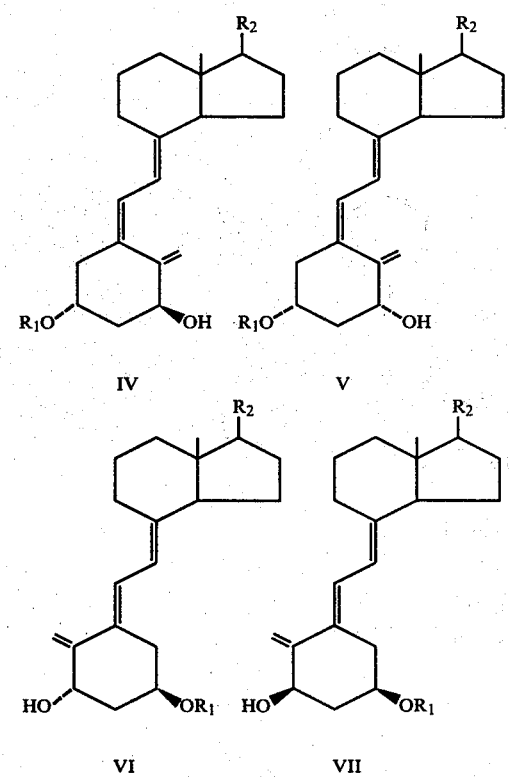

and separating the compound of formula VI from the second mixture, wherein $R_1$ is selected from the group consisting of hydrogen, trimethylsilyl, t-butyldimethylsilyl, phenyldimethylsilyl, acyl of from 2 to 6 carbon atoms, and aroyl wherein the aryl group is phenyl or substituted phenyl; $R_2$ is selected from the group consisting of

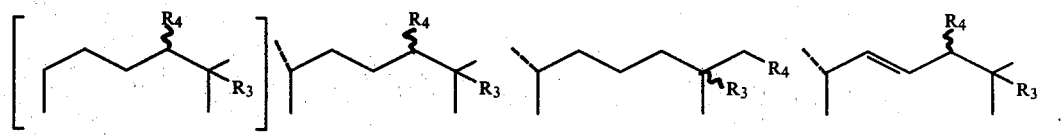

$R_3$ is selected from the group consisting of hydrogen, hydroxy, trimethylsilyloxy, acyloxy of from 2 to 6 carbon atoms, inclusive, aroyloxy; $R_4$ is selected from the group consisting of hydrogen, hydroxy, trimethylsilyloxy, t-butyldimethylsilyloxy, phenyldimethylsilyloxy, acyloxy of from 2 to 6 carbon atoms, inclusive, aroyloxy, and wherein R₃ and R₄ join to form a group selected from the group consisting of acetonide, carbonate and thiocarbonate, and

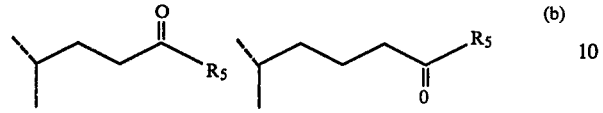

wherein R₅ is selected from the group consisting of hydrogen, methyl, hydroxyl and lower alkoxyl of from 1 to 5 carbon atoms, inclusive.

13. A process according to claim 12 wherein the compound prepared has the formula

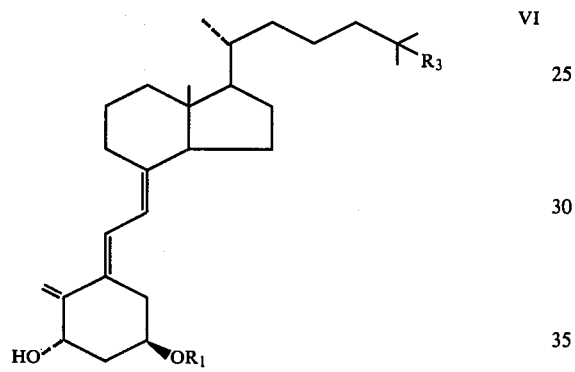

VI wherein R₁ is selected from the group consisting of aroyl, acyl and trimethylsilyl and R₃ is selected from the group consisting of hydrogen, hydroxy, trimethylsilyloxy and acyloxy of from 2 to 6 carbon atoms, inclusive.

14. A process according to claim 13 wherein R₃ is selected from the group consisting of trimethylsilyloxy and acyloxy of from 2 to 6 carbon atoms, inclusive.

15. A process according to claim 14 wherein R₁ is benzoyl and R₃ is trimethylsilyloxy.

16. A compound selected from the group consisting of

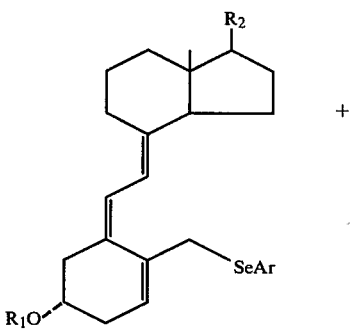

+

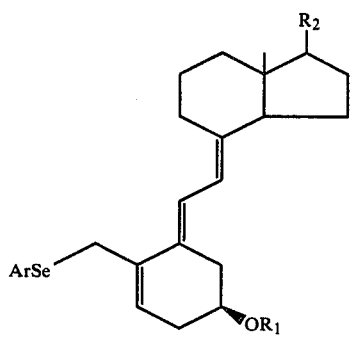

wherein R₂ is selected from the group consisting of

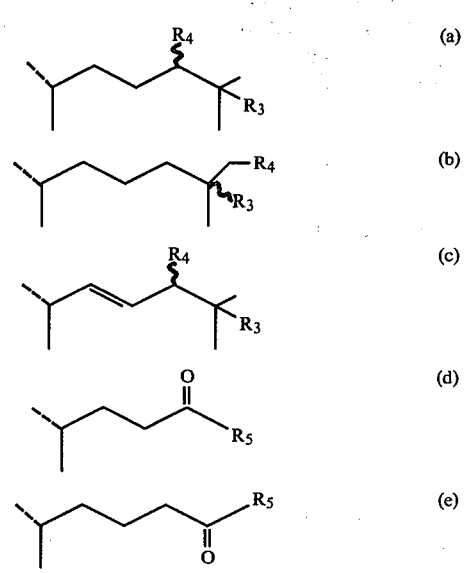

wherein R₁ is selected from the group consisting of hydrogen, trimethylsilyl, t-butyldimethylsilyl, phenyldimethylsilyl, acyl of from 2 to 6 carbon atoms, and aroyl wherein the aryl group is phenyl or substituted phenyl; R₃ is selected from the group consisting of hydrogen, hydroxy, trimethylsilyloxy, acyloxy of from 2 to 6 carbon atoms, inclusive, and aroyloxy. R₄ is selected from the group consisting of hydrogen, hydroxy, trimethylsilyloxy, t-butyldimethylsilyloxy, phenyldimethylsilyloxy, acyloxy of from 2 to 6 carbon atoms, inclusive, benzoyloxy, substituted benzoyloxy, and wherein R₃ and R₄ when taken together form a group selected from the group consisting of acetonide, carbonate and thiocarbonate; R₅ is selected from the group consisting of hydrogen, hydroxyl, methyl and lower alkoxy of from 1 to 6 carbon atoms, inclusive; and Ar is selected from the group consisting of phenyl and substituted phenyl.

17. A compound of claim 16 having the formula

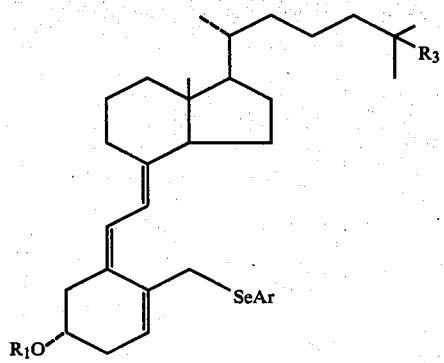

wherein Ar, R₁ and R₃ are the same as in claim 16.

18. A compound according to claim 16 wherein R₁ is selected from the group consisting of trimethylsilyl and aroyl and R₃ is selected from the group consisting of hydrogen, hydroxy, trimethylsilyloxy and acyloxy of from 2 to 6 carbon atoms and Ar is phenyl.

19. A compound according to claim 17 wherein R₁ is benzoyl and R₃ is hydrogen so that the specific embodiment is 19-phenylseleneno 9,10-secocholesta-1(10),5Z,7E-triene-3β-ol, 3-benzoate.

20. A compound according to claim 17 wherein R₁ is trimethylsilyl and R₃ is trimethylsilyloxy so that the specific embodiment is 19-phenylseleneno-9,10-secocholesta-1(10),5Z,7E-triene-3β-25-diol, 3,25-bis-trimethylsilylether.

21. A compound of claim 16 having the formula

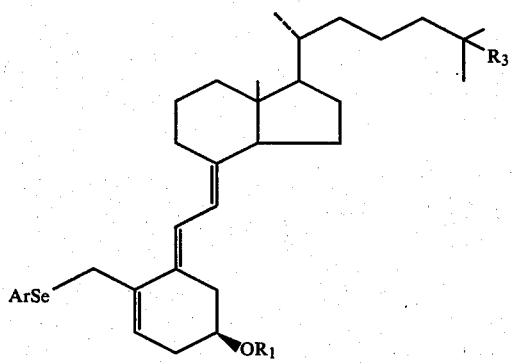

wherein Ar, R₁ and R₃ are the same as in claim 16.

22. A compound according to claim 21 wherein R₁ is selected from the group consisting of trimethylsilyl and aroyl; R₃ is selected from the group consisting of hydrogen, trimethylsilyloxy and acyloxy of from 2 to 6 carbon atoms and Ar is phenyl.

23. A compound according to claim 22 wherein R₁ is benzoyl and R₃ is trimethylsilyloxy so that the specific embodiment is 19-phenylseleneno-9,10-secocholesta-1(10),-5E,7E-triene-3β,25-diol, 3-benzoate, 25-trimethylsilylether.

24. A compound according to claim 22 wherein R₁ is benzoyl and R₃ is hydroxy so that the specific embodiment is 19-phenylseleneno-9,10-secocholesta-1(10),5E,7E-triene-3β,25-diol, 3-benzoate.

25. A compound according to claim 22 wherein R₁ is benzoyl and R₃ is acetoxy so that the specific embodiment is 19-phenylseleneno-9,10-secocholesta-1(10),5E,7E-triene-3β,25-diol, 3-benzoate, 25-acetate.

26. A process for preparing compounds having the formula

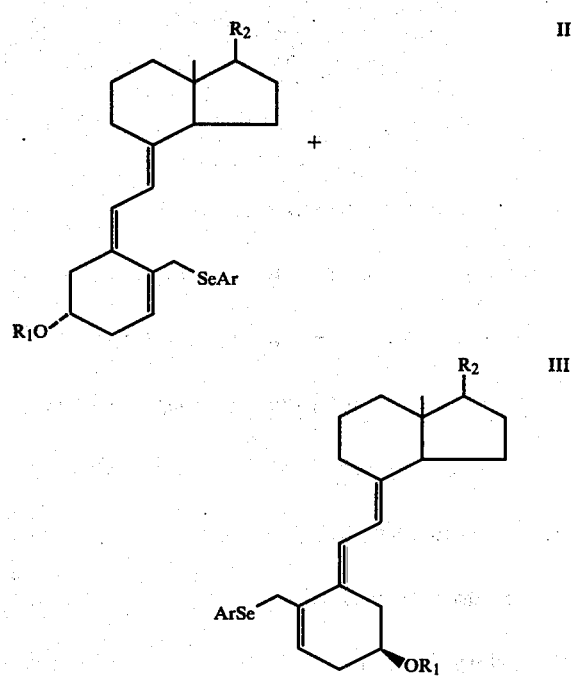

which comprises reacting compounds having the formula

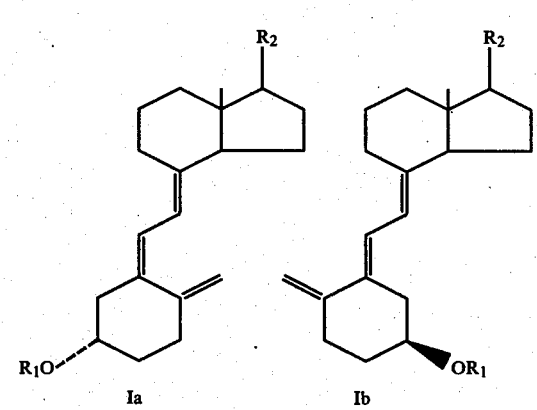

with a selenium reagent, wherein R₁ is selected from the group consisting of hydrogen, trimethylsilyl, t-butyldimethylsilyl, phenyldimethylsilyl, acyl of from 2 to 6 carbon atoms, and aroyl wherein the aryl group is phenyl or substituted phenyl; R₂ is selected from the group consisting of

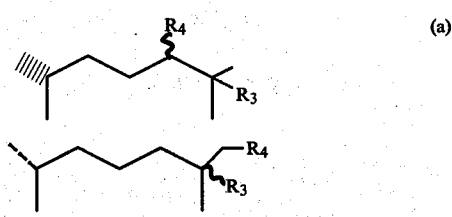

(a)

-continued

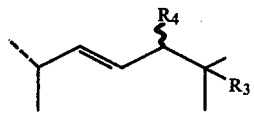

$R_3$ is selected from the group consisting of hydrogen, hydroxy, trimethylsilyloxy, acyloxy of from 2 to 6 carbon atoms, inclusive, benzoyloxy and substituted benzoyloxy; $R_4$ is selected from the group consisting of hydrogen, hydroxy, trimethylsilyloxy, t-butyldimethylsilyloxy, phenyldimethylsilyloxy, acyloxy of from 2 to 6 carbon atoms, inclusive, benzoyloxy and substituted benzoyloxy; wherein $R_3$ and $R_4$ join to form a group selected from the group consisting of acetonide, carbonate and thiocarbonate; and

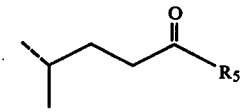

wherein $R_5$ is selected from the group consisting of hydrogen, methyl, hydroxyl and lower alkoxyl of from 1 to 5 carbon atoms, inclusive; and Ar is phenyl or substituted phenyl.

27. A process according to claim 26 for preparing a compound having the formula

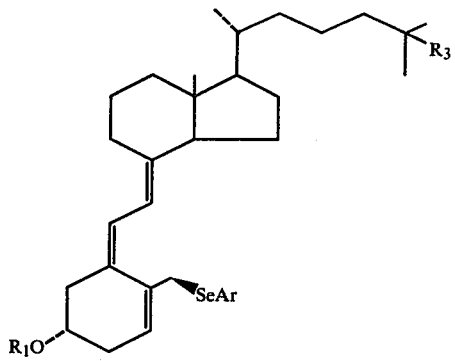

wherein Ar, $R_1$ and $R_3$ are the same as in claim 26.

28. A process according to claim 27 wherein $R_1$ is selected from the group consisting of trimethylsilyl and aroyl and $R_3$ is selected from the group consisting of hydrogen, hydroxy, trimethylsilyloxy and acyloxy.

29. A process according to claim 28 wherein $R_1$ is trimethylsilyl and $R_2$ is trimethylsilyloxy so that the specific embodiment is 19-phenylseleneno-9,10-seco-cholesta-1(10),5Z,7E-triene-3β-25-diol, 3,25-bis-trimethylsilylether.

30. A process according to claim 26 for preparing a compound having the formula

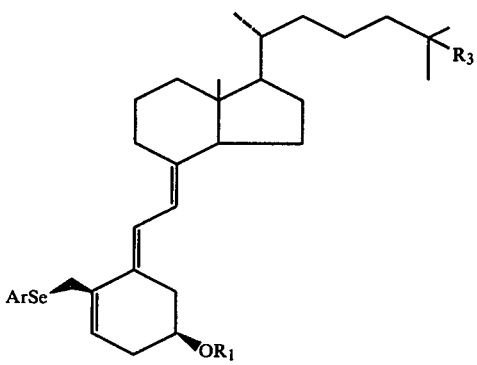

wherein $R_1$, $R_2$ and Ar are the same as in claim 25.

31. A process according to claim 7 wherein $R_1$ is benzoyl and $R_3$ is trimethylsilyloxy so that the compound prepared is 19-phenylseleno-9,10-secocholesta-1(10),5E,7E-triene-3β,25-diol, 3-benzoate, 25-trimethylsilylether.

32. A process according to claim 30 wherein $R_1$ is benzoyl and $R_3$ is acetoxy so that the compound prepared is 19-phenylseleno-9,10-secocholesta-1(10),5E,7E-triene-3β,25-diol, 3-benzoate, 25-acetate.

33. A process according to claim 30 wherein $R_1$ is benzoyl and $R_3$ is hydroxy so that the compound prepared is 19-phenylseleno-9,10-secocholesta-1(10),5E,7E-triene-3β,25-diol, 3-benzoate.

34. A process according to claim 30 wherein $R_1$ is benzoyl and $R_3$ is hydrogen so that the compound prepared is 19-phenylseleno-9,10-secocholesta-1(10),5E,7E-triene-3β-ol, 3benzoate.

* * * * *

UNITED STATES PATENT AND TRADEMARK OFFICE
CERTIFICATE OF CORRECTION

PATENT NO. : 4,206,131
DATED : June 3, 1980
INVENTOR(S) : William G. Salmond

It is certified that error appears in the above—identified patent and that said Letters Patent is hereby corrected as shown below:

Column 7, line 64: "3β-hydroxy" should read: -- 3β-hydroxyl --.

Column 22, line 51: "Example 3" should read: -- Example 8 --.

Column 20, line 49: "3.25-bis" should read: -- 3,25-bis --.

Column 29, lines 55-60: " 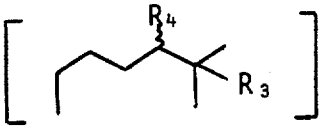 " should have been deleted prior to printing.

Column 33, line 18 (Claim 18): "A compound according to Claim 16" should read: -- A compound according to Claim 17 --.

Column 36, line 45 (Claim 30): "wherein $R_1$, $R_2$ and" should read: -- wherein $R_1$, $R_3$ and --.

Signed and Sealed this

Twenty-third Day of November 1982

[SEAL]

Attest:

GERALD J. MOSSINGHOFF

Attesting Officer

Commissioner of Patents and Trademarks